(12) United States Patent
Ritchart et al.

(10) Patent No.: US 6,428,486 B2
(45) Date of Patent: Aug. 6, 2002

(54) METHODS AND DEVICES FOR AUTOMATED BIOPSY AND COLLECTION OF SOFT TISSUE

(75) Inventors: Mark A. Ritchart, Murrieta; J. Michael Stuart, Lake Forest; Fred H. Burbank, San Juan Capistrano; Kenneth M. Galt, Seal Beach, all of CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/746,402

(22) Filed: Dec. 21, 2000

Related U.S. Application Data

(60) Division of application No. 08/825,899, filed on Apr. 2, 1997, now abandoned, which is a division of application No. 08/386,941, filed on Feb. 10, 1995, now Pat. No. 5,649,547, which is a continuation-in-part of application No. 08/217,246, filed on Mar. 24, 1994, now Pat. No. 5,526,822.

(51) Int. Cl.$^7$ .................................................. A61B 5/00
(52) U.S. Cl. ...................................................... 600/566
(58) Field of Search ....................... 600/562, 564–567; 606/167, 170

(56) References Cited

U.S. PATENT DOCUMENTS

| | | | |
|---|---|---|---|
| 2,705,949 A | 4/1955 | Silverman | 128/2 |
| 2,919,692 A | 1/1960 | Ackerman | 128/2 |
| 3,342,175 A | 9/1967 | Bulloch | 128/2 |
| 3,404,667 A | 10/1968 | Springer | 128/2 |
| 3,590,808 A | 7/1971 | Muller | 128/2 B |
| 3,606,878 A | 9/1971 | Kellogg, Jr. | 128/2 B |
| 3,732,858 A | 5/1973 | Banko | 128/2 B |
| 3,734,099 A | 5/1973 | Bender et al. | 128/305 |
| 3,844,272 A | 10/1974 | Banko | 128/2 B |
| 4,099,518 A | 7/1978 | Baylis et al. | 128/2 B |
| 4,200,106 A | 4/1980 | Douvas et al. | 128/305 |
| 4,203,444 A | 5/1980 | Bonnell et al. | 128/276 |
| 4,210,146 A | 7/1980 | Banko | 128/305 |
| 4,243,048 A | 1/1981 | Griffen | 128/751 |
| 4,306,570 A | 12/1981 | Matthews | 128/754 |
| 4,393,872 A | 7/1983 | Reznik et al. | 604/151 |
| 4,461,305 A | 7/1984 | Cibley | 128/754 |
| 4,517,977 A | 5/1985 | Frost | 128/305 |
| 4,600,014 A | 7/1986 | Beraha | 128/754 |
| 4,644,951 A | 2/1987 | Bays | 128/305 |
| 4,651,753 A | 3/1987 | Lifton | 128/751 |
| 4,681,213 A | 7/1987 | Valtchev | 128/753 |
| 4,699,154 A | 10/1987 | Lindgren | 128/754 |
| 4,702,260 A | 10/1987 | Wang | 128/753 |
| 4,702,261 A | 10/1987 | Cornell et al. | 128/754 |
| 4,708,147 A | 11/1987 | Haaga | 128/753 |
| 4,729,764 A | 3/1988 | Gualtier | 604/38 |
| 4,733,671 A | 3/1988 | Mehl | 128/754 |
| 4,735,215 A | 4/1988 | Goto et al. | 128/754 |
| 4,781,202 A | 11/1988 | Janese | 128/754 |

(List continued on next page.)

FOREIGN PATENT DOCUMENTS

| | | | |
|---|---|---|---|
| DE | 935 625 | 11/1955 | |
| EP | 0378 692 A1 | 7/1990 | A61B/17/36 |
| EP | 0442 851 B1 | 12/1990 | A61B/17/32 |
| WO | WO93/14707 | 8/1993 | A61B/17/32 |
| WO | WO93/22972 | 3/1998 | A61B/17/068 |

Primary Examiner—Max Hindenburg

(57) ABSTRACT

Instruments for performing percutaneous biopsy procedures are disclosed, which have advantageous features for improving functionality and performance over prior art devices. These instruments comprise two types, single-use devices, and multiple-use devices having active tissue capture capability. Improved features include the ability to retrieve and evaluate multiple tissue samples during a single insertion procedure, without physical handling of the samples, as well as constructional features, such as a molded tissue cassette housing, variant vacuum port embodiments suited for different tissue environments, and a method for backflushing the instrument to remove biological debris, among others.

4 Claims, 11 Drawing Sheets

U.S. PATENT DOCUMENTS

| | | | |
|---|---|---|---|
| 4,844,088 A | 7/1989 | Kambin | 128/753 |
| 4,850,373 A | 7/1989 | Zatloukal et al. | 128/749 |
| 4,893,635 A | 1/1990 | De Groot et al. | 128/754 |
| 4,919,146 A | 4/1990 | Rhinehart et al. | 128/752 |
| 4,924,878 A | 5/1990 | Nottke | 128/752 |
| RE33,258 E | 7/1990 | Onik et al. | 604/22 |
| 4,940,061 A | 7/1990 | Terwilliger et al. | 128/754 |
| 4,944,308 A | 7/1990 | Akerfeldt | 128/751 |
| 4,958,625 A | 9/1990 | Bates et al. | 128/754 |
| 4,966,583 A | 10/1990 | Debbas | 604/98 |
| 4,971,067 A | 11/1990 | Bolduc et al. | 128/751 |
| 4,976,269 A | 12/1990 | Mehl | 128/754 |
| 4,991,592 A | 2/1991 | Christ | 128/754 |
| 5,005,585 A | 4/1991 | Mazza | 128/754 |
| 5,031,634 A | 7/1991 | Simon | 128/754 |
| 5,048,538 A | 9/1991 | Terwilliger et al. | 128/754 |
| 5,108,381 A | 4/1992 | Kolozsi | 604/319 |
| 5,111,828 A | 5/1992 | Kornberg et al. | 128/754 |
| 5,125,413 A | 6/1992 | Baran | 128/754 |
| 5,133,359 A | 7/1992 | Kedem | 128/754 |
| 5,133,360 A | 7/1992 | Spears | |
| RE34,056 E | 9/1992 | Lindgren et al. | 128/754 |
| 5,174,300 A | 12/1992 | Bales et al. | 128/751 |
| 5,183,052 A | 2/1993 | Terwilliger | 128/753 |
| 5,183,054 A | 2/1993 | Burkholder et al. | 128/754 |
| 5,188,118 A | 2/1993 | Terwilliger | 128/753 |
| 5,195,533 A | 3/1993 | Chin et al. | 128/754 |
| 5,197,484 A | 3/1993 | Kornberg et al. | 128/754 |
| 5,224,470 A | 7/1993 | Schneep-Pesch et al. | 128/753 |
| 5,224,488 A | 7/1993 | Neuffer | 128/751 |
| 5,234,000 A | 8/1993 | Hakky et al. | 128/754 |
| 5,243,994 A | 9/1993 | Rannalletta | 128/754 |
| 5,249,583 A | 10/1993 | Mallaby | 128/754 |
| 5,254,129 A | 10/1993 | Alexander | 606/170 |
| 5,255,688 A | 10/1993 | Gillard | 128/753 |
| 5,282,476 A | 2/1994 | Terwilliger | 128/753 |
| 5,284,156 A | 2/1994 | Schramm et al. | 128/754 |
| 5,301,684 A | 4/1994 | Origala | 128/754 |
| 5,313,958 A | 5/1994 | Bauer | 128/754 |
| 5,316,013 A | 5/1994 | Stiebel, II et al. | 128/754 |
| 5,320,110 A | 6/1994 | Wang | 128/753 |
| 5,324,300 A | 6/1994 | Elias et al. | 606/180 |
| 5,333,619 A | 8/1994 | Burgio | 128/754 |
| 5,335,672 A | 8/1994 | Bennett | 128/754 |
| 5,336,176 A | 8/1994 | Yoon | 604/51 |
| 5,341,816 A | 8/1994 | Allen | 128/754 |
| 5,348,022 A | 9/1994 | Leigh et al. | 128/754 |
| 5,353,804 A | 10/1994 | Kornbery et al. | 128/754 |
| 5,368,045 A | 11/1994 | Clement et al. | 128/754 |
| 5,526,822 A | 6/1996 | Burbank et al. | 128/754 |
| 5,538,008 A | 7/1996 | Crowe | 128/751 |
| 5,573,008 A * | 11/1996 | Robinson et al. | 600/567 |
| 5,649,547 A | 7/1997 | Ritchart et al. | 128/754 |

* cited by examiner

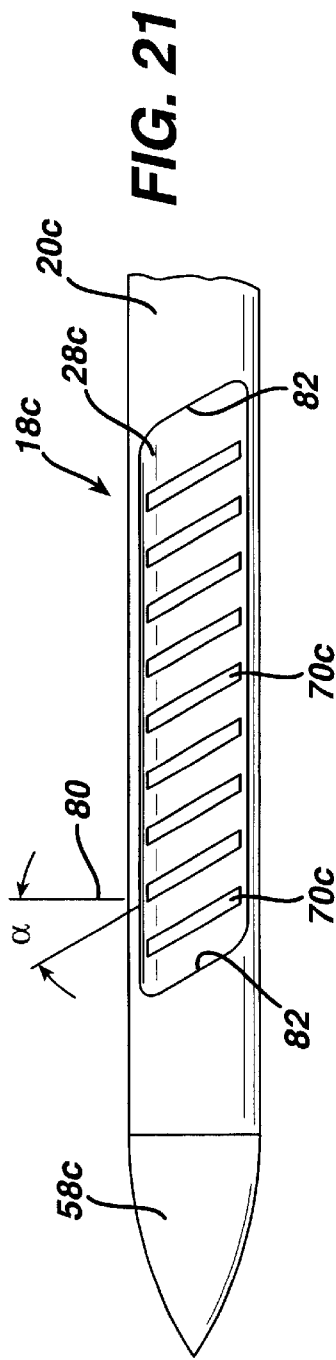
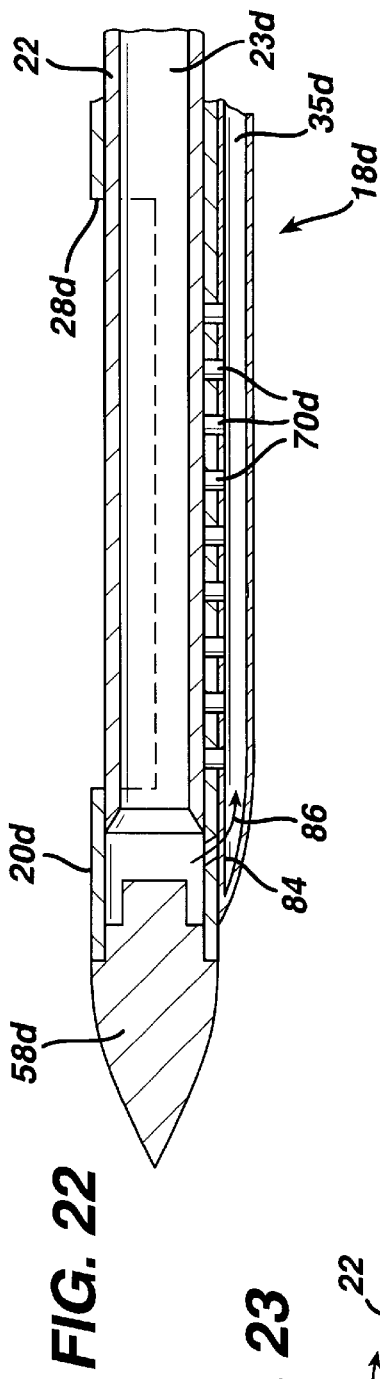
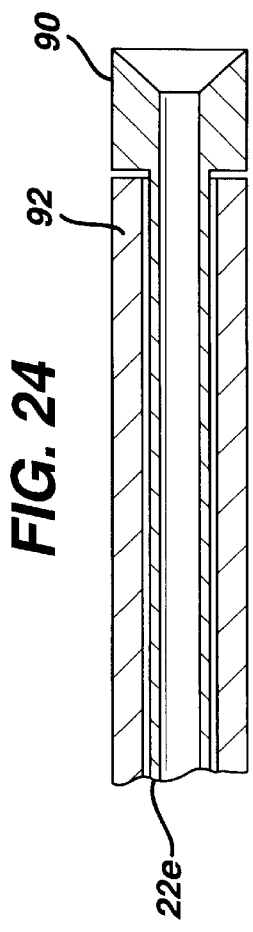
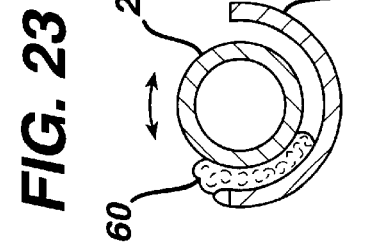

METHODS AND DEVICES FOR AUTOMATED BIOPSY AND COLLECTION OF SOFT TISSUE

CROSS-REFERENCE TO RELATED APPLICATIONS

This application is a DIV of application Ser. No. 09/825,899, filed Apr. 2, 1997, now abandoned, which is a DIV of application Ser. No. 09/386,941, filed Feb. 10, 1995, now U.S. Pat. No. 5,647,547 which is a continuation-in-part of parent application Ser. No. 08/217,246, filed Mar. 24, 1994, now U.S. Pat. No. 5,526,822.

FIELD OF THE INVENTION

The present invention relates to methods and devices for tissue sampling, and more specifically to improved biopsy instruments and methods for acquiring subcutaneous biopsies and for removing lesions.

BACKGROUND OF THE INVENTION

It is often desirable and frequently necessary to sample or test a portior tissue from humans and other animals particularly in the diagnosis and treatment of patients with cancerous tumors, premalignant conditions, and other diseases or disorders. Typically, in the case of cancer, when the physician establishes by means of procedures such as palpation, x-ray, or ultrasound imaging that suspicious circumstances exist, a biopsy is performed to determine whether the cells are cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, and no single procedure is ideal for all cases. However, core biopsy is extremely useful in a number of conditions and is being used more frequently by the medical profession.

Two types of image guided percutaneous core breast biopsy instruments are presently available. One such instrument is a spring-powered single-use device, such as the BIOPTY® gun, available from C. R. Bard, Inc. Such a gun is shown and described in U.S. Pat. Nos. 4,699,154 and 4,944,308, as well as in U.S. Reissued Pat. No. Re. 34,056, all of which are herein expressly incorporated by reference. These devices are useful because of their inexpensive construction, enabling them to be economically used for only a single patient, and because they are lightweight and easy to use. However, they also have disadvantages. An important disadvantage is that the small core size makes it necessary to accurately place the needle when sampling small lesions. To sample a lesion thoroughly, many separate insertions must be made. Each time a new sample is taken, the device must be removed, and the breast or organ must be punctured again upon re-insertion of the device. This action is tedious and time consuming.

A further disadvantage of such single-use guns is the needle typically used in such a device, e.g. the True Cut® needle manufactured by Travenol Laboratories. This needle optimally allows a roughly cylindrical shaped sample of tissue, termed a "core", to be obtained from a pointed, side cutting device, percutaneously, and comprises a pointed inner stilette with a side-facing notch to receive tissue near its distal pointed end and an outer, sharpened sliding cannula. In operation, once the lesion is targeted, the inner stilette is thrust into the organ or lesion of interest. Tissue passively prolapses into the side facing notch and the outer cannula is rapidly advanced, thereby severing the sample of tissue contained within the notch. Unfortunately, the True Cut® needle is rough on organs and lesions, often only obtaining small fragments of tissue, and is quite operator dependent—some individuals are good at operating the device and some are not. It also is tissue selective, meaning that the piercing stilette and sliding cutter can "push away" the lesion of interest, particularly in situations where a relatively large lesion is surrounded by much softer tissue (i.e. fat).

The second type of image guided percutaneous core breast biopsy instrument currently available is a vacuum-assisted automatic core biopsy device. One such successful biopsy gun is shown and disclosed in related parent application Ser. No. 08/217,246, filed on Mar. 24, 1994, which is commonly owned by the assignee of the present application and is herein incorporated by reference. This gun has the capability to active capture tissue prior to cutting the tissue. Active capture allows for sampling through non-homogeneous tissues, meaning that the device is equally capable of cutting through hard and soft tissue. The gun also includes means to direct and position the cutting chamber in arbitrary positions about and along its longitudinal axis, means for rapid and atraumatic removal of an arbitrary number of core samples with only a single needle insertion into the body and organ, and means for coding and decoding the location from which the samples were obtained. Together, these capabilities allow for more complete sampling of large lesions and for the complete removal of small lesions. This type of instrument has been very successful in permitting the obtainment of a plurality of tissue samples from different locations with only a single needle insertion, as well as in obtaining high quality samples in a manner which does not require direct handling of the samples by the operator. However, it does not operate equally well in all procedures and in all bodily environments. For example, instrument performance and success often varies dependent upon the type of body tissue being sampled; i.e. relatively fatty or relatively hard.

What is needed then, are innovations for improving the quality and completeness of the tissue sample obtained using a single-use core biopsy instrument, as well as constructional improvements and variants with respect to the active capture type of instrument which will permit it to operate with maximum efficiency and to operate equally well in all tissue environments.

SUMMARY OF THE INVENTION

This invention addresses the aforementioned needs by providing a number of important new features and innovations for the active capture type of biopsy instrument which each collectively or singly contribute to improved and more versatile operation. For example, such innovations include a molded tissue cassette housing, permitting easy and inexpensive fabrication while also permitting the handling and viewing of multiple tissue samples without physical contact by the instrument operator. The housing is interconnected with the piercing needle using a thumbwheel which permits the needle to rotate relative to the housing, thereby preventing the vacuum tube from wrapping about the housing. Several variant vacuum port embodiment are disclosed, each of which have advantages in certain tissue environments. Also disclosed is a method for backflushing biological debris from the instrument which builds up after repeated sampling procedures, without removing the instrument from the selected tissue location.

With respect to the single-use type of biopsy instrument, several tissue capture embodiments are disclosed for improving the capture process, so that complete and well preserved samples are obtained. Many of these embodiments are also applicable for use with the active capture instrument type.

More particularly, in one aspect of the invention, a biopsy instrument is provided which comprises a housing and a needle assembly, wherein the needle assembly includes a tubular piercing member having a distal pointed end and a laterally positioned tissue receiving port proximate to the distal pointed end which opens into a tissue sample chamber. The tubular piercing member is rotatably attached to the housing and held in an axially fixed position within a selected tissue mass. The needle assembly further includes a cannular cutting member adapted to coact with the tubular piercing member to cut a tissue sample from the tissue mass. The tissue sample is transported to a proximate end of the tubular piercing member by the cutting member as it is withdrawn proximally along the tubular piercing member. An elongate knock-out pin is disposed coaxially within the tubular piercing member and the cannular cutting member for the primary purpose of dislodging the tissue sample from the cutting member at a predetermined location as the cutting member is withdrawn.

Surprisingly, the inventors have found that preferably, in order to minimize tissue clogging of the cutter, the knock-out pin should have an effective diameter or cross-sectional area of at least 0.030 inches, and the ratio of the effective diameter of the knock-out pin to the internal diameter of the cannular cutter should be at least approximately one-half.

In another aspect of the invention, a biopsy instrument includes an elongate hollow outer piercing needle having a lumen, a sharpened distal end for piercing tissue, and a lateral opening located proximal to the sharpend distal end for receiving a portion of a tissue mass positioned adjacent to the lateral opening. Also included are an elongate inner cutting cannula having a lumen, which is disposed coaxially and slidably within the outer piercing needle. The inner cannula has a sharpened distal end for cutting the portion of tissue protruding into the lateral opening of the outer piercing needle when the inner cannula slides distally past the lateral opening. This causes the portion of cut tissue to be deposited within the inner cannula proximal to the distal end. A vacuum generator generates a vacuum pressure which fluidly communicates with the lateral opening through the inner cannula lumen. In such an embodiment, it is often desirable to prevent the tissue sample from migrating proximally through the cutting cannula lumen, so an inventive tissue stop device is disposed in the lumen of the inner cannula which has a structure, preferably a corkscrew portion of a linear wire, disposed proximally of the lateral opening. This structure sufficiently obstructs the lumen so that the tissue sample cannot migrate proximally past it.

In yet another aspect of the invention, a biopsy instrument includes an outer hollow cannula having a distal end portion which comprises a plurality of leaflets. Each leaflet has a proximal end which is hinged to the outer cannula wall and a distal end, and are each biased to pivot about their hinges to a closed position wherein the distal ends of the leaflets contact one another. The instrument further includes an inner hollow cannula, and at least one of the inner and outer cannulas is slidable relative to the other cannula, so that first the inner cannula may be extended distally with respect to the outer cannula to force the leaflets to an open position, and to cut and contain a tissue sample, and then the outer cannula may be extended distally with respect to the inner cannula sufficiently so that the leaflets clear the inner cannula and snap closed about their hinges, thereby severing the tissue sample and containing it within the inner cannula.

In a further aspect of the invention, a biopsy instrument has an outer hollow cannula having a sharpened distal end portion and an inner hollow cannula having a distal portion which is biased to expand radially at its distal end. At least one of the cannulas is slidable relative to the other cannula, so that fit the inner cannula may be extended distally with respect to the outer cannula, such that the inner cannula distal portion expands radially to capture a tissue sample. Then the outer cannula may be extended distally with respect to the inner cannula sufficiently so that the distal end portion of the inner cannula is forced by the outer cannula to close about and sever the tissue sample, thereby containing the sample within the inner cannula. The distal portion of the inner cannula may comprise, for example, either an alligator tip having a pair of hinged jaws which are biased to expand radially, or a plurality of hooked extractors.

Still another aspect of the invention involves a method for flushing debris form a biopsy instrument, which includes an outer piercing needle having a laterally positioned tissue receiving port which opens into a tissue receiving chamber and an inner cutting cannula having an axial lumen and a sharpened distal end, which is disposed coaxially and slidably within the outer piercing needle. Further included in the biopsy instrument is a vacuum lumen disposed beneath the tissue receiving port which further comprises at least one fluid communication port disposed distally of the distal end of the inner cannula when the inner cannula is in its fully advanced position. The inventive method includes the steps of advancing the inner cannula of the instrument so that it extends distally sufficiently to completely close off the tissue receiving port and then injecting a pressurized fluid through one of the inner cannula and the vacuum lumens, so that the fluid flows through the fluid communication port and into the other one of the two lumens, from which the fluid returns to its source, thereby flushing accumulated debris from the biopsy instrument.

The invention, together with additional features and advantages thereof, may best be understood by reference to the following description taken in conjunction with the accompanying illustrative drawing.

BRIEF DESCRIPTION OF THE DRAWING

FIG. 21 is a top plan schematic view of the tissue receiving port of a fourth modified needle assembly embodiment;

FIG. 22 is a cross-sectional view similar to FIG. 3, illustrating a fifth modified needle assembly embodiment;

FIG. 23 is a cross-sectional view through the tissue port of a needle assembly like that shown in FIG. 5, illustrating a potential tissue binding situation under certain operating regimes;

FIG. 24 is a fragmentary cross-sectional view of the cutter portion of a sixth modified needle assembly embodiment, illustrating an inventive solution to prevent potential tissue binding situations like that illustrated in FIG. 23;

FIG. 25 is a cross-sectional view of a prior art single-use biopsy device, of the type shown and described in U.S. Pat. No. 4,699,154;

DESCRIPTION OF THE INVENTION

Figure 1:
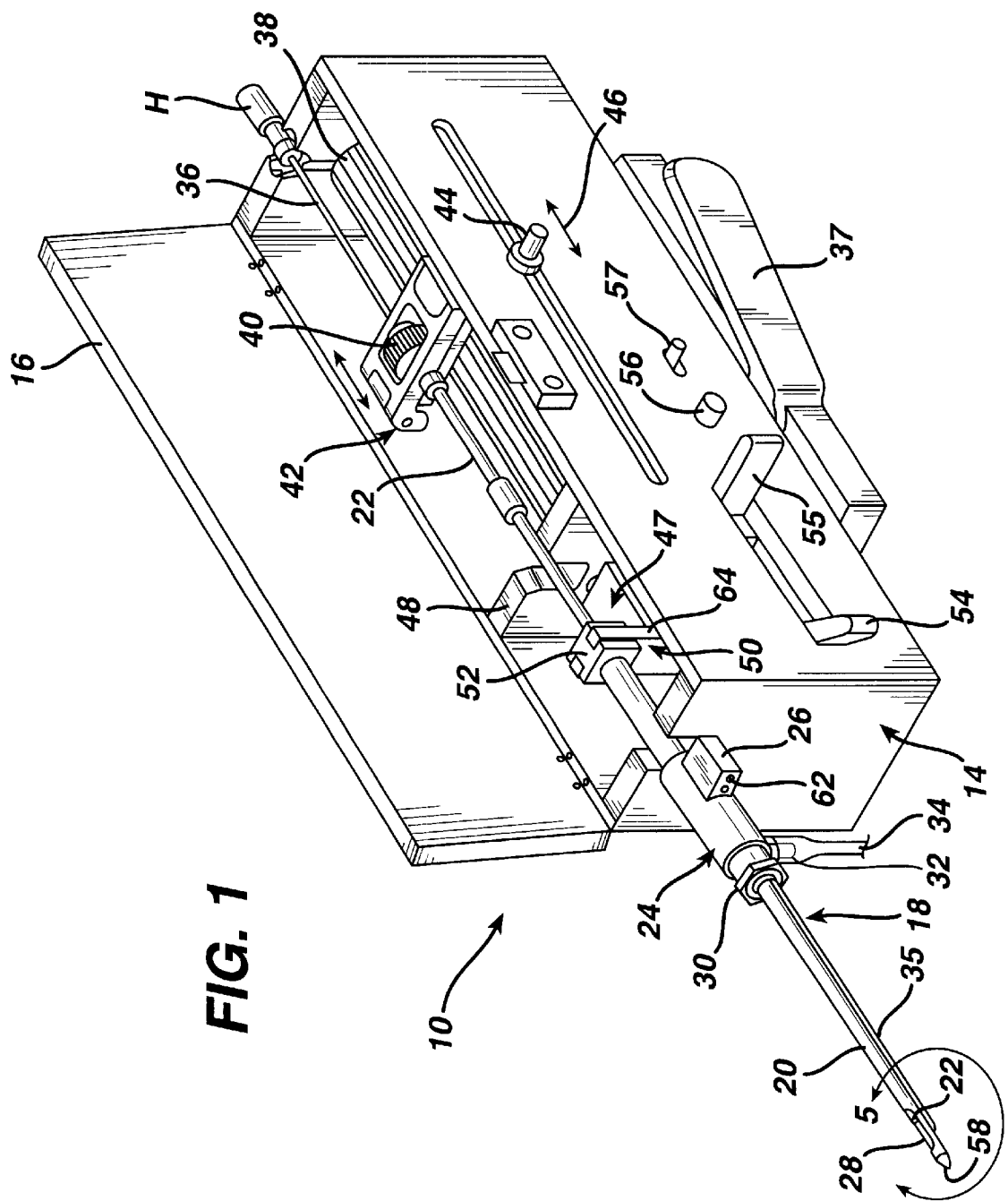
FIG. 1 is a perspective view of an automatic core biopsy device of the type shown and described in co-pending patent application Ser. No. 08/217,246.
Figure 4:
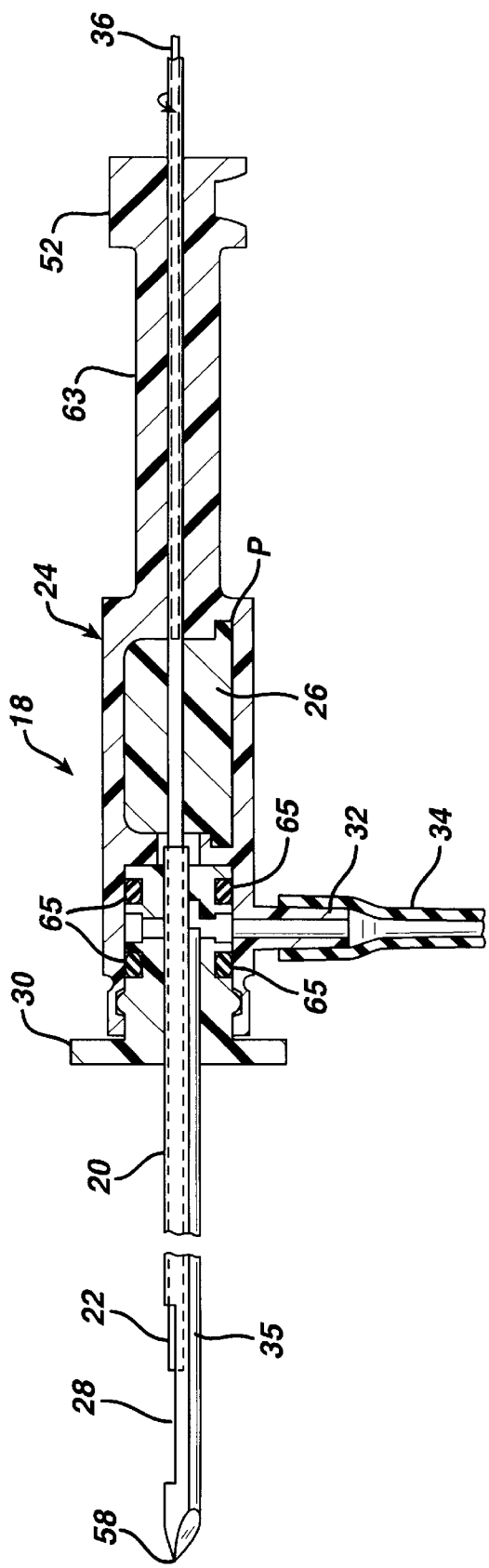
FIG. 4 is a cross-sectional view, from the left side, of the needle assembly of the device illustrated in FIG. 1.
Figure 5:
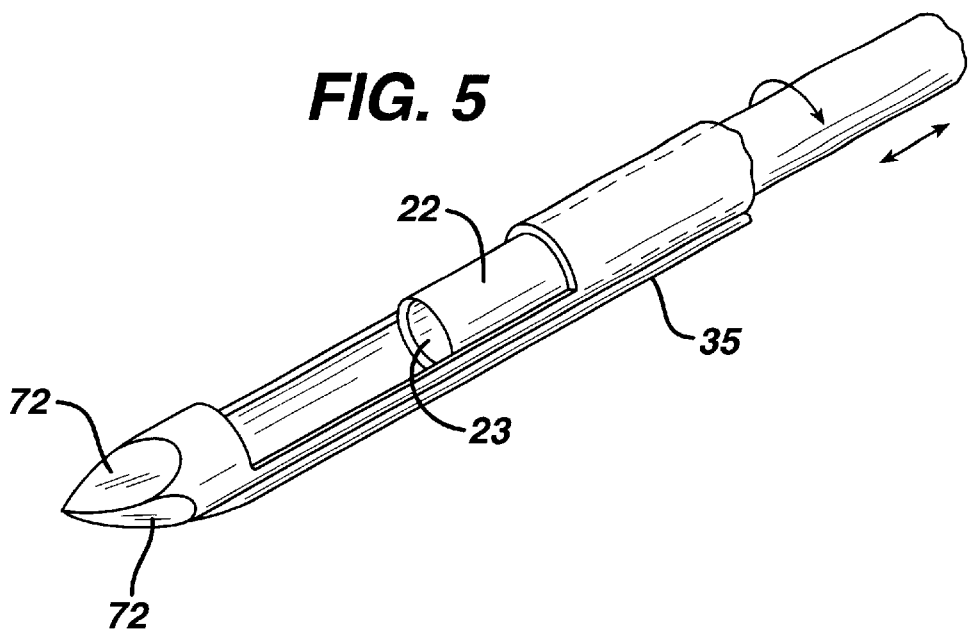
FIG. 5 is an enlarged perspective view of the portion of FIG. 1 delineated by the numeral 5.

Referring now to FIGS. 1, 4, and 5, a preferred embodiment of an automatic core biopsy device 10 of the tape disclosed in related patent application Ser. No. 08/217,246 is illustrate. The illustrated biopsy instrument 10 comprises a housing 14 having a hinged lid 16. A needle assembly 18 extends out of the housing 14, and comprises a hollow outer piercing needle 20, an inner cutter 22 having a lumen 23 (FIG. 5), a tissue cassette housing 24, and a tissue cassette 26. The hollow outer piercing needle 20 further includes a tissue receiving port or bowl 28. A thumbwheel 30 interconnects the tissue cassette housing 24 and the hollow outer piercing needle 20, preferably permitting rotation of the needle 20 without rotating the tissue cassette housing 24, as will be more completely described hereinbelow. A vacuum port 32 in the tissue cassette housing 24 is adapted for attachment to a vacuum source through a tube or tubing 34, in order to provide a vacuum at the tissue receiving port or bowl 28. Preferably, the vacuum is supplied through a separate vacuum lumen 35, but may alternatively or simultaneously be supplied directly through the lumens of the hollow outer piercing needle 20 and the inner cutter 22, respectively, if desired.

Telescopically and coaxially arranged within the hollow outer piercing needle 20 and the inner cutter 22 is a knock-out pin 36. It is mounted to be stationary, and is preferably fabricated of stainless steel, but may also be constructed of other biocompatible materials, such as plastic. The pin 36 preferably is tubular, and the hub H of the knock-out pin serves as a secondary vacuum port which supplies the vacuum through the needle 20 and inner cutter 22. Surprisingly, Applicants have found that it is important to appropriately size the knock-out pin to minimize clogging problems. For this reason, it has been found that, for the preferred embodiment where the inner diameter of the outer piercing needle 20 is approximately 0.074 inches and the inner diameter of the inner cutter 22 is approximately 0.063 inches, the effective diameter of the knock-out tube 36, meaning the cross-sectional area of the tube, should be at least approximately 0.030 inches. Preferably, the effective diameter of the knock-out tube is about 0.045 inches.

The biopsy instrument housing 14 contains the driving mechanisms and controls for operating the needle assembly 18, and may be mounted in a stationary fashion on a base 37. This base 37 may be an integral part of the housing 14 and is preferably designed to mate with an I-beam rail of a stereotactic imaging unit, but may be modified and designed to match and mate with any of the various imaging units available in the industry. The driving mechanisms for the illustrated preferred embodiment include a long spur gear 38 and a cutter drive gear 40, which is housed within a pinion housing 42 and is rotatably and drivingly attached to the inner cutter 22 within the housing 14. In order to rotate or oscillate the cutter 22, the gear 38 is rotated by a driving motor or stepper motor (not shown). Rotation or oscillation of the gear 38 in turn drives the gear 40 to rotate or oscillate, thereby rotating or oscillating the cutter 22.

In addition to rotation or oscillation, the cutter 22 may also be driven to travel axially, both distally and proximally. A slide handle 44, which is attached along with the pinion housing 42 to a slide (not shown), may be actuated by an operator in either direction, as illustrated by the arrow 46, to drive the pinion housing 42 axially. Since the cutter 22 is fixedly attached to the pinion gear 40, which in turn is contained within the pinion housing 42, the cutter follows the axial travel of the pinion housing, permitting the operator to advance or retract the cutter, as desired.

A piercing mechanism or linear actuator 47, located distally of a partition 48 in the housing 14, functions to rapidly advance the entire needle assembly 18 distally in order to locate the tip of the outer piercing needle 20 at the site from which one or more tissue samples are desired. The piercing mechanism preferably includes a driving spring (not shown), a carriage assembly 50, which is attached to a proximal end portion 52 of the tissue cassette housing 24, a cocking lever 54 which operates against a fixed lever 55, a pierce button 56, and a safety button 57. Operation of the piercing mechanism is described in greater detail hereinbelow.

Of course the illustrated embodiment is just one of many possible ways to drive and control an automatic core biopsy device of the type shown and described. For example, the control system could be an integral part of the computer system in the stereotactic or other imaging device used to guide the biopsy device, so that the stereotactic device computer would be used to control the cutter, the angular and longitudinal position of the piercing needle 20, and the knock-out tube position. Additionally, different driving mechanisms could be employed, such as substituting a friction drive for the long spur gear drive. In some instances it may be preferred to be able to rotatably and linearly drive and control the hollow outer piercing needle and the knock-out pin, as well as the inner cutter, as disclosed in co-pending application Ser. No. 08/217,246, or to employ one of the other needle assembly or needle assembly driving arrangement embodiments disclosed therein. Of course, any of the embodiments disclosed in that application may also be used in conjunction with the inventions herein disclosed.

Figure 2:
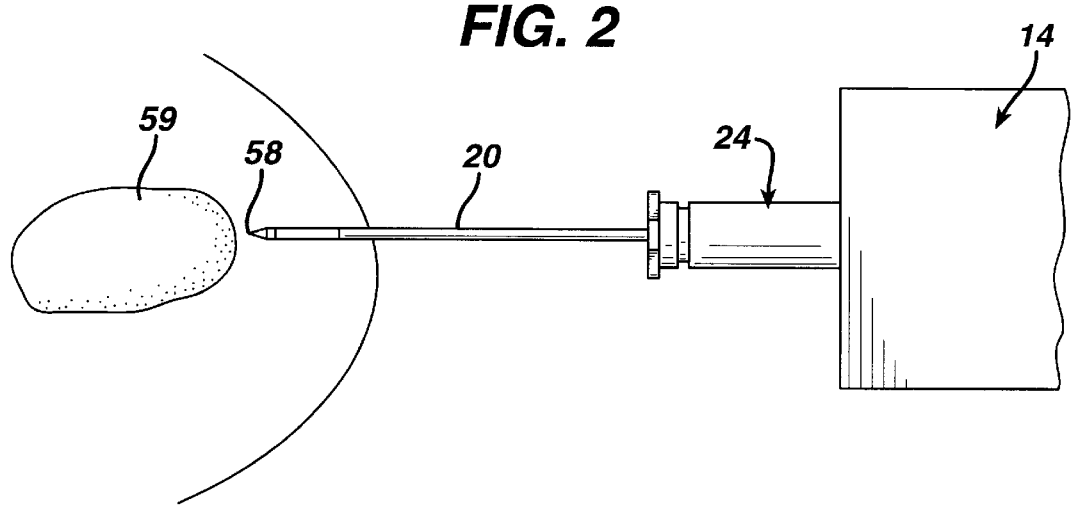
FIG. 2 is a schematic plan view, from the left side, of a portion of the needle assembly of the device illustrated in FIG. 1, showing the device before it penetrates a target lesion.
Figure 3:
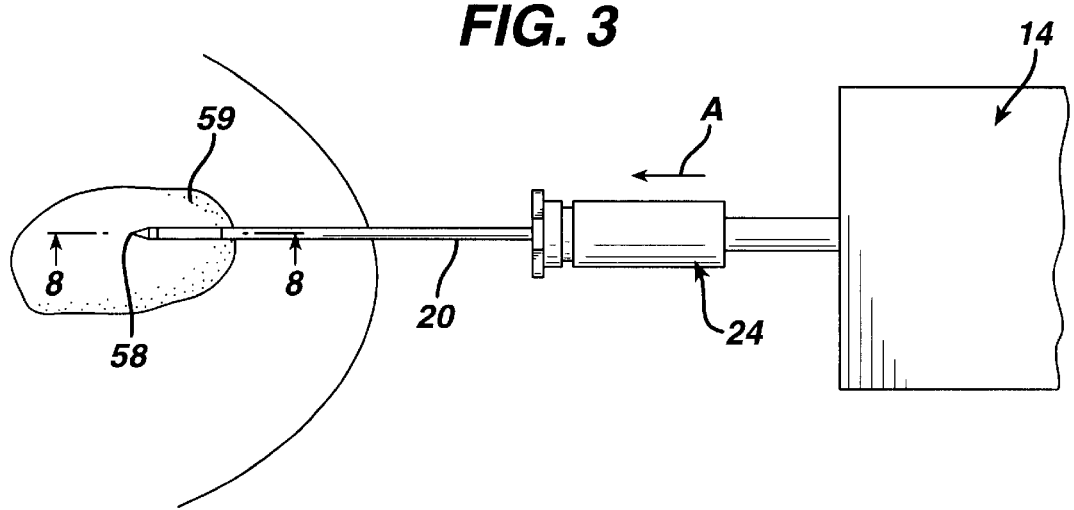
FIG. 3 is a schematic plan view similar to FIG. 2, showing the device after it has penetrated the target lesion, in a position to begin collecting tissue samples.

In operation, as described in the aforementioned co-pending application and with particular reference to FIGS. 2, 3, and 8 through 13, in addition to FIGS. 1, 4, and 5, the point 58 of the needle 20 is first moved into position to pierce the lesion or selected tissue which is to be sampled (FIGS. 2 and 3). The initial global position of the point 58 with respect to the tissue area being sampled is determined by the overall position of the biopsy inset 10 with respect to the patient. For example, the biopsy instrument 10 may be mounted on a commercially available stereotactic guidance system (not shown), commonly used in the medical field for accurate positioning of a variety of medical devices with respect to a patient and with respect to a lesion within a patient. A detailed description of such a motorized biopsy needle positioner, i.e. a stereotactic guidance system, is given in U.S. Pat. No. 5,240,011, issued on Aug. 31, 1993, to Michael Assa, which is hereby incorporated herein by reference. The suspect lesion 59 within the tissue to be sampled is targeted according to the instructions provided with the stereotactic guidance system. The stereotactic guidance system will enable an operator to advance the point 58 until it is adjacent the specific lesion region 59 to be sampled, as illustrated in FIG. 2.

Once the point 58 is adjacent to the specific lesion region to be sampled, fine tuning of the location of the point 59 within the tissue sample is preferably accomplished by actuating the linear actuator 47 to thereby advance and retract the hollow outer piercing needle 20 along its axis (the actuator 47 may, however, be used for rapid piercing as well). While the linear actuator 47 illustrated in FIG. 1, which uses a potential energy device (spring), is preferred, any of a variety of devices capable of inducing linear motion may be employed, including solenoids, pneumatic cylinders, or potential energy devices such as springs, motors, or the like. In operation of the preferred embodiment, the cocking lever 54 is pulled proximally against the fixed lever 55 to compress the spring and cock the carriage assembly 50 in its proximal position, as shown in FIG. 2. Then, when the needle 20 is positioned outside the lesion, as illustrated in FIG. 2, the pierce button 56 is depressed, releasing the carriage housing 50 so that the spring uncoils, forcing it rapidly in the direction of the arrow A (FIG. 3), such that the point 58 of the needle pierces the lesion 59. Alternatively, this procedure could be automated, using a needle control unit to send signals to the linear actuator, which, in turn, would advance and react the hollow outer piercing needle 20 along its axis.

Figure 8:
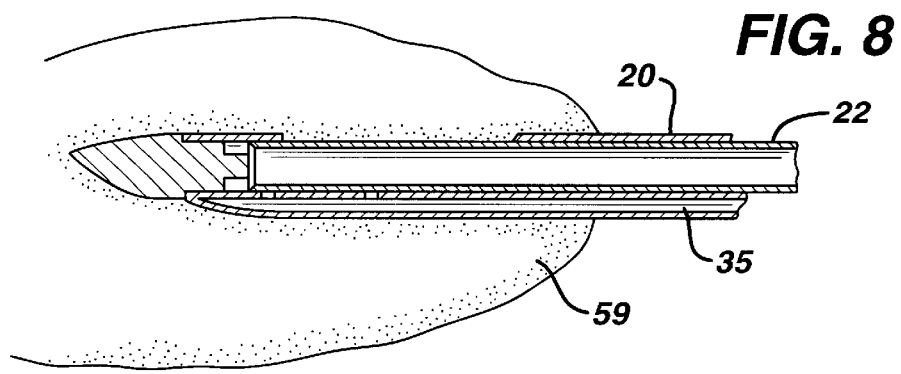
FIG. 8 is an enlarged cross-sectional view taken along lines 8—8 of FIG. 3.
Figure 9:
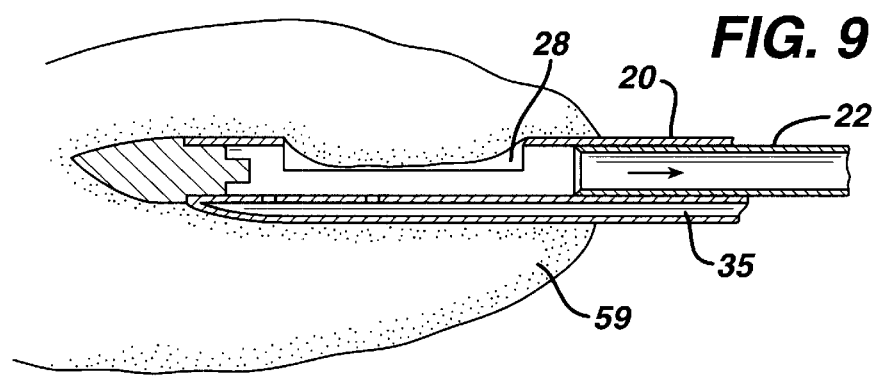
FIG. 9 is an enlarged cross-sectional view similar to FIG. 8, illustrating the withdrawal of the cutter after insertion of the needle into the target lesion.
Figure 10:
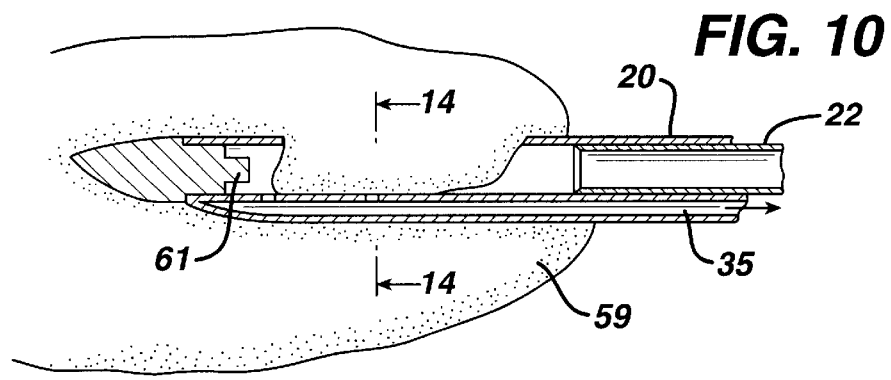
FIG. 10 is an enlarged cross-sectional view similar to FIG. 8, illustrating the prolapse of tissue into the tissue receiving port following the application of the vacuum pressure.

Now with particular reference to FIGS. 8–13, as seen in FIG. 8, the needle 20 is preferably advanced into the lesion 59 with the inner cutter 22 in its fully advanced position to close off the tissue receiving port 28, thus preventing snagging and tearing of the tissue during slow linear movement of the needle 20. After the hollow outer piercing needle 20 has been positioned at the precise location within the lesion 59 at which it is desired to obtain a tissue sample, a vacuum source is actuated to apply a vacuum to the vacuum connection 32 in the tissue cassette housing 24 through the vacuum tube 34 (FIG. 1) as the cutter is retracted proximally (FIGS. 9 and 10). As a result, a region of low pressure is generated within the hollow outer piercing needle 20 in the vicinity of the tissue receiving port 28, and through the vacuum lumen 35. This facilitates the prolapse of tissue immediately adjacent to the tissue receiving port 28 into the interior of the hollow outer piercing needle 20.

Figure 11:
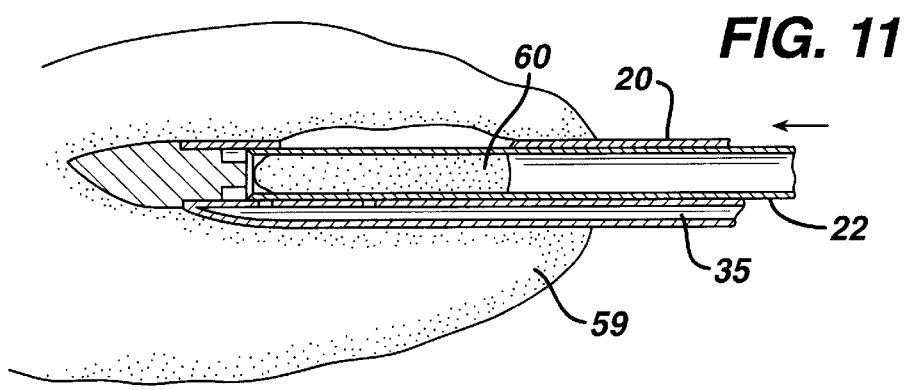
FIG. 11 is an enlarged cross-sectional view similar to FIG. 8, illustrating the simultaneous rotation and distal advancement of the cutter to cut off a tissue sample.
Figure 12:
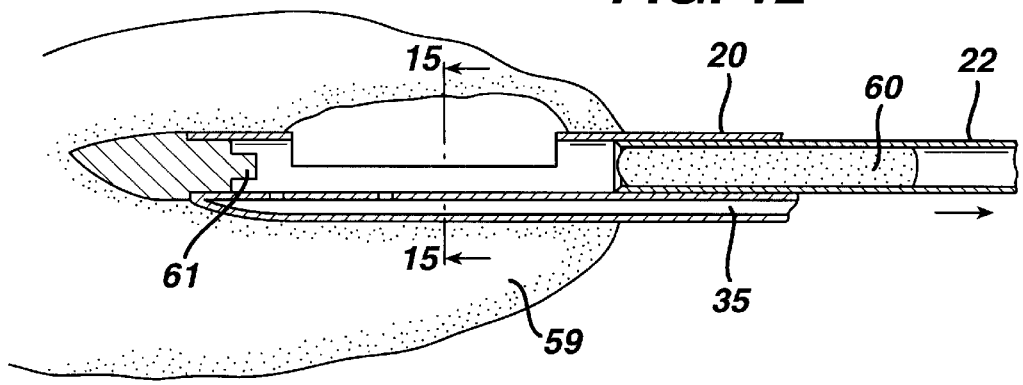
FIG. 12 is an enlarged cross-sectional view similar to FIG. 8, illustrating the proximal withdrawal of the cutter with the tissue sample contained therein.
Figure 13:
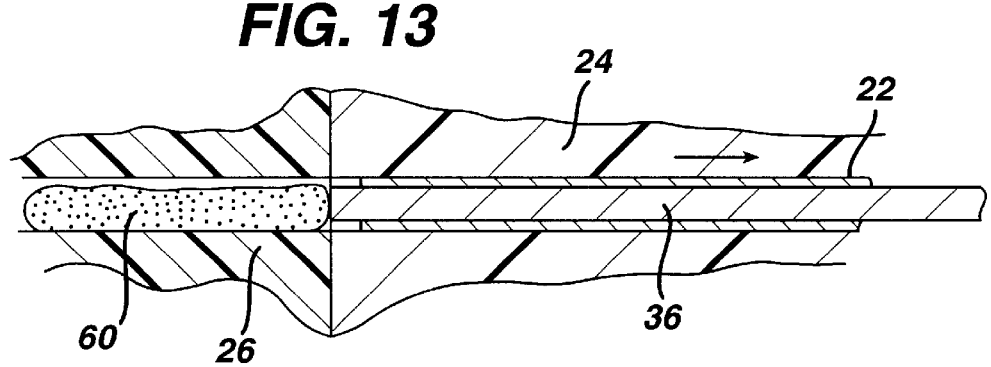
FIG. 13 is an enlarged cross-sectional view of the interface between the proximal end of the tissue cassette and the tissue cassette housing illustrated in FIG. 4, showing the operation of the knock-out pin to retain the tissue sample in the tissue cassette as the cutter is withdrawn proximally.

Once the tissue is fully prolapsed into the tissue receiving port, as shown in FIG. 10, the prolapsed tissue sample 60 is severed from the main tissue mass by the advancement of the cannular inner cutter 22 (FIG. 11). The advancement of the inner cutter 22 is achieved by advancing the slide knob 44 attached to the pinion housing 42, thus advancing the inner cutter 22 along its axis within the hollow outer piercing needle 20 past the tissue receiving port 28, to thereby sever the prolapsed tissue sample from the main tissue mass. After being severed from the tissue mass, the tissue sample is packed into the inner cutter as it moves forward against the needle pin 61 and rests inside the inner cutter 22. The inner cutter 22, containing the tissue sample 60, is then withdrawn by retracting the slide knob 44 (FIG. 12). The tissue sample is held in the inner cutter 22 as it is withdrawn proximally toward the tissue cassette housing 24 by friction with the inner walls of the cannula Suction created by the vacuum source can also be used to retain the sample.

As the inner cutter 22 is withdrawn through the tissue cassette housing 24, the tissue sample 60 is deposited into the tissue cassette 26 by means of the tubular knock-out pin 36, the distal end of which stops the tissue sample within one of the tissue containment chambers 62 (FIG. 1), as is more fully described in the related application Ser. No. 08/217,246. Once the tissue cassette 26 is filled with tissue samples, it may be removed from the tissue cassette housing 24 and transported to a laboratory for analysis, without the necessity of handling the samples. If additional samples are desired, a new tissue cassette 26 may be immediately inserted into the tissue cassette housing 24 and the collection of samples may continue.

Referring now to FIG. 4, the needle assembly 18 of FIG. 1 is illustrated in greater detail. Significantly, the preferred embodiment of the needle assembly comprises a two-piece body, including the hollow outer piercing needle 20, with its inner cutter 22 and knock-out pin 36, and the tissue cassette housing 24. The frame of the tissue cassette housing 24 (excluding the cassette 26) is preferably molded from a single piece of plastic. If clear plastic is used, an additional advantage is the resultant ability to view the collected tissue specimens in the cassette, which is located in a cassette port P in the housing 24 during operation of the device. Magnification of the specimen is obtained by molding the top surface of the housing 24 to be convex, while the inner surface is substantially flat. The preferred one-piece plastic cassette housing 24 includes a shaft portion 63, which provides a conduit for holding the cutter 22 and the knockout pin 36, and the proximal end portion 52, which in turn is adapted to be mounted on a post 64 within the housing 14 (FIG. 1), forming a part of the carriage assembly 50. This portion of the cassette housing thus provides the support for the entire cantilevered needle assembly 18.

Figure 14:
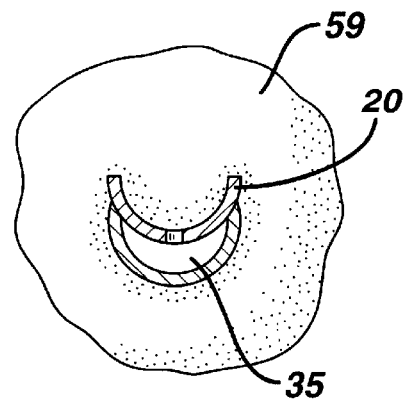
FIG. 14 is a cross-sectional view taken along lines 14—14 of FIG. 10.
Figure 15:
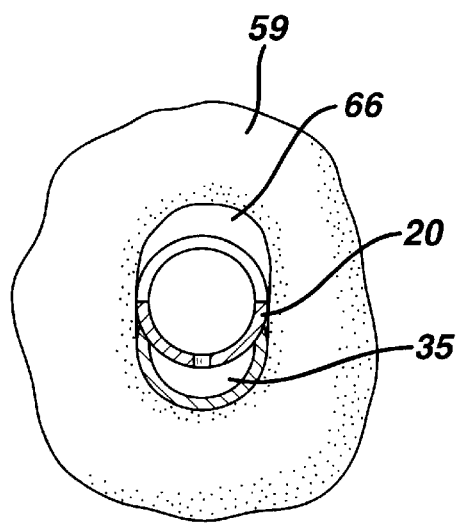
FIG. 15 is a cross-sectional view taken along lines 15—15 of FIG. 12.
Figure 16:
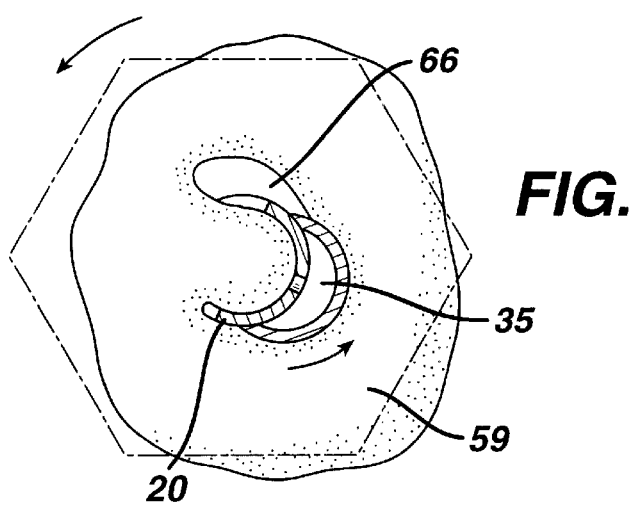
FIG. 16 is a cross-sectional view similar to FIG. 14, wherein the outer needle and inner cutter have been rotated approximately 90 degrees counterclockwise to take a second tissue sample.

Yet another advantageous feature of the preferred needle assembly 18 is the thumbwheel 30. The needle 20 is glued or otherwise securely attached to the thumbwheel, which is then snapped into the housing 24. O-rings 65 fluidly seal the interface between the housing 24 and the thumbwheel 30, in order to preserve the vacuum between the port 32 and the vacuum lumen 35 while simultaneously permitting rotation of the thumbwheel relative to the fixed housing 24. Because of this inventive feature, the vacuum may be communicated to the needle 20 from the vacuum port 32 in the housing 24 no matter what the orientation of the needle is, without the problem sometimes encountered in prior embodiments wherein the vacuum tube 34 wraps about the housing 24 as it rotates with the needle 20. The ability to keep the cassette housing 24 stationary solves this hose wrap problem FIGS. 14–17 illustrate a procedure enabled by the thumbwheel 30, whereby four tissue samples 60 may be acquired from four different angular positions and deposited in the sample cassette 26 without removing the hollow outer piercing needle 20 and the tissue receiving port 28 from the lesion 59. Furthermore, the integrity of each sample may be preserved and a record of the location from which each of the four samples is acquired may be created by storing the samples in individual sample containment chambers 62 (FIG. 1). FIG. 14 is a cross-sectional view along lines 14—14 of FIG. 10, which illustrates preparations for the taking of a first sample 60 (FIG. 11) with the needle 20 and associated vacuum lumen 35 angularly oriented so that the tissue receiving port is in an upright position within the lesion 59. FIG. 15 is a cross-sectional view along lines 15—15 of FIG. 12, wherein the needle 20 is angularly oriented in the same position as in FIG. 14, after the tissue sample has been removed. The void 66 represents the location from which the sample was taken FIG. 16 shows the needle assembly as illustrated in FIGS. 14 and 15, but where the thumbwheel 30 (FIG. 4) has been used to rotate the needle 20 approximately 90 degrees counterclockwise. A second sample is to be taken from this angular location.

Figure 17:
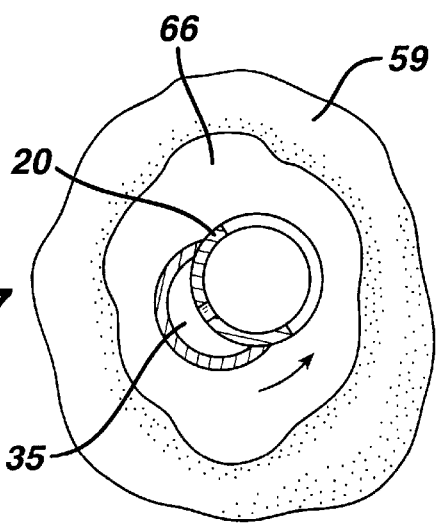
FIG. 17 is a cross-sectional view similar to FIG. 15, wherein the outer needle and inner cutter have been rotated approximately 300 degrees counterclockwise, and a fourth tissue sample has been taken.

Finally, FIG. 17 is yet another similar view, wherein the needle 20 has been rotated by the thumbwheel 30 approximately 300 degrees counterclockwise from the original orientation shown in FIGS. 14 and 15 (it should, however, be noted that the invention permits samples to be taken from any angular orientation between 0 and 360 degrees). A sample has already been taken from this orientation, as well as from the 180 degree orientation, so that the void 66 now extends entirely about the needle assembly and four tissue samples have been removed.

Figure 18:
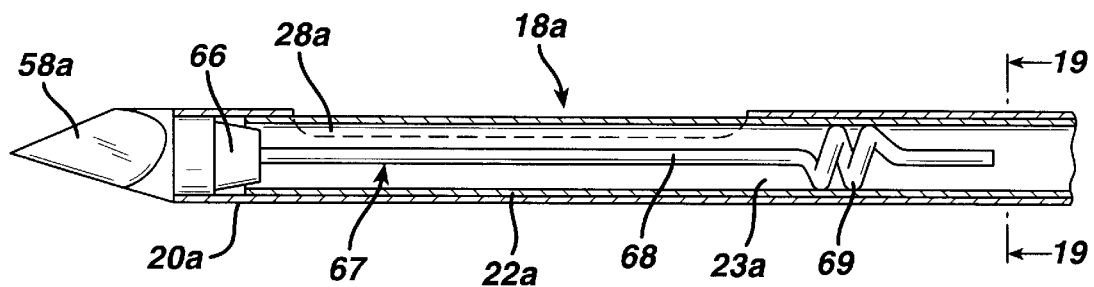
FIG. 18 is a cross-sectional view of a second embodiment of the needle assembly shown in FIG. 3.
Figure 19:
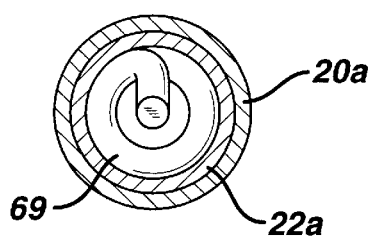
FIG. 19 is a cross-sectional view along lines 19—19 of FIG. 18.

Now with reference to FIGS. 18 and 19, a modified embodiment of a portion of the needle assembly 18 of FIGS. 1, 4, and 5 is illustrated, wherein like elements are designated with like reference numerals, followed by the letter a. This needle assembly embodiment may be used in conjunction with a vacuum which is drawn through the cutter lumen 23a, and particularly in a procedure where the physician wishes to obtain only a single sample and wants to retain the tissue sample in the tissue receiving port 28a for retrieval (i.e. a "single-core" procedure).

Attached to the proximal end of the needle point 58a is a distal tip 66 of a tissue stop or wire assembly 67, which comprises a wire 68 which is integral with and extends proximally of the tip 66. The attachment of the point 58a to the tip 66 is preferably made by brazing though other equivalent known attachment methods may be used as well. The wire 68 extends beneath the entire axial length of the tissue receiving port 28a. Proximally of the tissue receiving port 28a, and near the proximal end of the wire 68, is a corkscrew portion 69, which has a diameter or cross-sectional width just slightly less than the internal diameter of the inner cutter 22a, as illustrated in FIG. 19.

In operation, with the cutter 22a withdrawn proximally from the region of the tissue receiving port 28a, the wire assembly 67 is stationary in the lumen of the hollow outer piercing needle 20a. With the needle in position in the tissue to be sampled, a vacuum is drawn through the cutter lumen 23a and the needle lumen, thereby prolapsing tissue into the tissue receiving bowl 28a. A potential problem is that such tissue will prolapse all the way to the bottom of the bowl at a proximal region of the bowl, thereby cutting off the vacuum distally of the blocking portion. Without the vacuum, the distal portion of the bowl may not receive a full volume of prolapsed tissue, thereby causing the tissue sample, when cut, to be only a partial sample. However, the wire 68 functions to hold the prolapsed tissue in an elevated position above the bottom of the bowl, thereby preventing blockage of the lumen. This permits the vacuum to be transmitted all the way to the tip 66 so that a full-volume sample is assured.

Once the prolapsed tissue sample has been received, and cut off by the inner cutter 22a, the corkscrew portion 69 functions to prevent the sample from being sucked or pulled out of the bowl 28a during withdrawal of the cutter. Then, after the needle is withdrawn from the patient's body and the cutter 22a is withdrawn from the bowl 28a, the tissue sample remains in the bowl and may be retrieved directly from the bowl by the physician or an assistant.

In one preferred embodiment the inner diameter of the hollow outer piercing needle 20a was 0.074 inches, and the inner diameter of the inner cutter 22a was 0.063 inches. The diameter of the wire 68 was 0.014 inches, and the diameter or cross-sectional width of the corkscrew portion 69 was 0.060 inches. Of course, many other dimensions may be utilized as well. Additionally, while a corkscrew configuration is preferred, many other configurations may be employed, as long as they function to prevent proximal migration of the tissue sample, especially during withdrawal of the cutter. For example, a simple kink in the wire may be used, instead.

Figure 6:
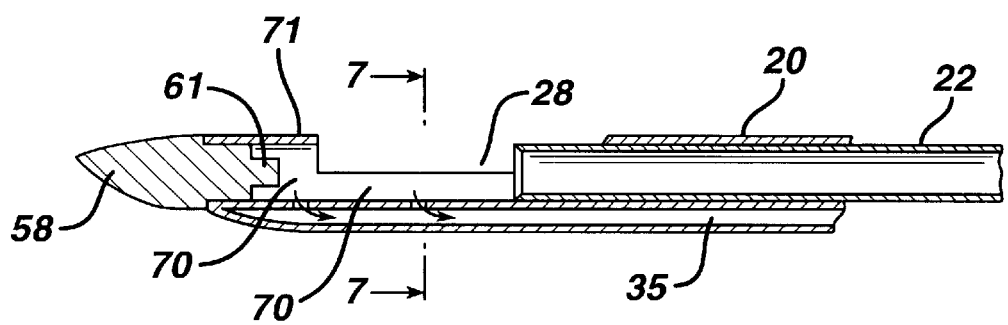
FIG. 6 is a cross-sectional view of one embodiment of the needle assembly illustrated in FIG. 5.
Figure 7:
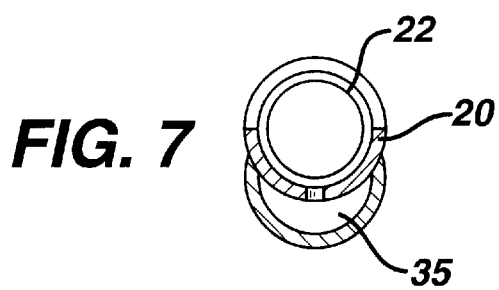
FIG. 7 is a cross-sectional view taken along lines 7—7 of FIG. 6.

Now with particular reference to FIGS. 5 and 6, the distal portion of the needle assembly illustrated in FIGS. 1 and 4 is shown in perspective and in cross-section, respectively. Two particular features not previously discussed are of note. First, in this particular embodiment, two preferably round vacuum ports 70 communicate between the tissue receiving port 28 and the vacuum lumen 35. The distal port 70 is located distally of the tissue receiving port opening, so that it lies just proximally of the point 58 and beneath overhang portion 71 of the needle 20. In the preferred embodiment, it has a diameter of approximately 0.042 inches. The proximal port 70, on the other hand is significantly smaller, preferably about one-half the diameter of the larger port (approximately 0.020 inches), and lies directly beneath the tissue receiving port 28.

The second feature of note is related to how the needle point is ground for sharpening. As illustrated in FIG. 5, it is preferred that the point be ground to form a plurality of facets 72 (preferably three) wherein no two facets axially intersect within the circumferential are defined by the tissue receiving port 28. Thus, the needle point 58 defines a relatively flat surface on its upper side, as illustrated. This is advantageous in that the flat top surface 72 lifts the tissue upwardly and thereby assists its entry into the tissue receiving port 28. On the other hand, if two of the facets 72 axially intersect within the arc defined by the tissue receiving port, the tissue often tends to split, potentially degrading the sample quality.

Figure 20:
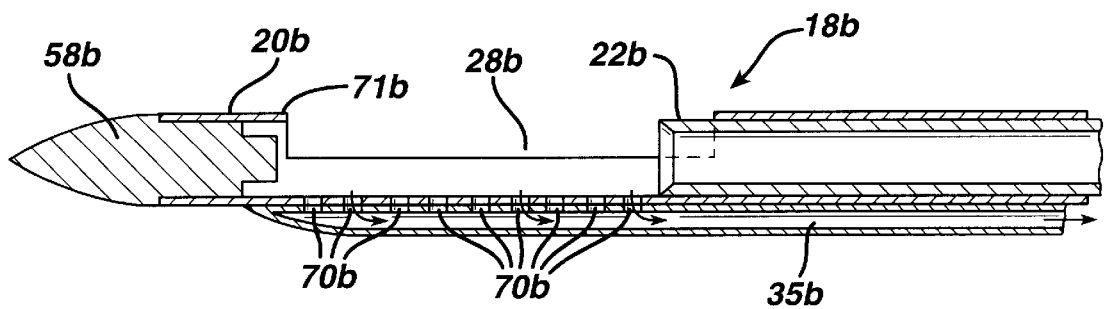
FIG. 20 is a cross-sectional view of a third embodiment of the needle assembly shown in FIG. 3.

Referring now to FIG. 20, a modified embodiment of the needle assembly 18 illustrated in FIG. 6 is shown, wherein like elements are designated by like reference numerals, followed by the letter b. The primary difference between this embodiment and that of FIG. 6 is the employment of a greater number of vacuum ports 70b, preferably eight, between the vacuum lumen 35b and the tissue receiving port 28b. In this embodiment, preferably each of the ports 70b is round and has a diameter of approximately 0.042 inches. Also, in this embodiment all of the ports are located beneath the opening of the tissue receiving port, as illustrated. None lie beneath the overhang portion 71b.

The reason for the two different vacuum port configurations in FIGS. 6 and 20 is that each has advantages over the other when sampling certain types of tissue. For example, in relatively fatty tissue, the eight hole embodiment illustrated in FIG. 20 may have a greater tendency to clog. Clogging sometimes occurs when numerous samples are being taken because, as tissue is received into the tissue receiving port, the vacuum drawn through the vacuum ports 70b tends to draw tissue past the ports and into the vacuum lumen 35b. Then, when the cutter 22b advances to sever the tissue sample, small pieces of tissue within the vacuum ports fall into the vacuum lumen 35b. Over many sampling cycles, the tissue buildup in the vacuum lumen 35b partially blocks the vacuum to the distal ports, causing an uneven and diminished overall vacuum pressure and thereby reducing the quality of the tissue samples being obtained. The two-port embodiment illustrated in FIG. 6 avoids this problem, because the single small port subject to contact with the tissue sample prolapsing into the tissue receiving port is so small that even if tissue does fall into the vacuum lumen from this port, it does not build into a mass sufficient to cause a blockage. The distal port, on the other hand, is protected by the overhang 71 from contact with the tissue, so no tissue can become caught in the port to create clogging.

When relatively hard tissue is being sampled, in contrast, the eight-port embodiment shown in FIG. 20 may be preferable. This is because hard tissue is less pliable, and therefore generally requires a more evenly distributed vacuum pressure to draw it fully into the tissue receiving port. Obviously, the higher number of evenly spaced ports in the FIG. 20 embodiment will provide this necessary drawing pressure. Furthermore, hard tissue is much less likely to actually be drawn into the vacuum ports 70b, so clogging is not a likely issue.

FIG. 21 illustrates a further modified embodiment of the needle assembly 18 illustrated in FIG. 6, wherein like elements are designated by like reference numerals, followed by the letter c. The difference between the FIGS. 6, 20, and 21 embodiments is that in FIG. 21, the vacuum ports 70c are arranged at an angle α with respect to the transverse axis 80 of the needle assembly 18c. Additionally, the side walls 82 of the tissue receiving port 28c are preferably arranged at substantially the same angle α. In the preferred embodiment, the angle α is approximately 15–75 degrees. This angled orientation is advantageous because it permits the cutter 22c (not shown in FIG. 21) to traverse the vacuum ports 70c and side walls 82 of the tissue receiving port 28c more easily and minimizes damage to the cutter blade due to interfering contact with these edges.

Yet another modified embodiment of the needle assembly embodiment illustrated in FIG. 6 is shown in FIG. 22. In this embodiment, like elements are designated by like reference numerals, followed by the letter d.

The FIG. 22 embodiment is designed to assist in solving the clogging problem discussed with respect to the FIGS. 6 and 20 embodiments and sometimes encountered during the process of collecting a number of tissue samples from a patient during a single procedure. As previously discussed, the problem is that bits of tissue, blood, and other biological debris will, over time, become detached from the tissue samples being collected and become lodged in the tissue receiving port 28d, vacuum ports 70d, or in one of the lumens 23d or 35d. Since the vacuum ports 70d are relatively small, the problem of clogging those ports is most acute, as the resultant reduced vacuum in the tissue receiving port 28d may cause the collection of partial tissue samples. Consequently, as illustrated in FIG. 22, a flush port 84 may be located between the vacuum lumen 35d and the piercing needle lumen, similar to vacuum ports 70d but located distally of the closed (most advanced) position of the cutter 22*d*. Then, when the cutter 22*d* is in the closed position, as illustrated, a pressurized saline solution may be permitted to flow through the cutter lumen 23*d* into the needle lumen distally of the cutter, then through the flush port 84 as shown by the arrow 86, and finally returned to its source through the vacuum lumen 35*d*. This procedure clears any accumulated debris and thus helps to ensure that the tissue samples are as complete as possible. A safety feature prevents saline from being injected through the system when the cutter is not in a fully closed position; i,e. completely blocking the tissue receiving port 28*d*.

As illustrated in FIG. 23, a problem sometimes encountered during operation of the biopsy device 10 (FIG. 1) is that the tissue sample 60 being pulled into the tissue receiving port or bowl 28 may have a tendency to bind as the relatively large cross-section of tissue is necked down into the space between the rotating cutter 22 and the needle 20. This problem is worsened because of the possible rotation of the cutter 22 relative to the stationary needle 20. In FIG. 24, a solution to this problem is illustrated, wherein the cutter 22*e* is modified to comprise a relatively short blade portion 90, and a non-rotating sleeve 92, preferably comprising a polyamide or a similar low-friction material or coating, surrounds the remainder of the cutter and translates axially with it. The sleeve thus acts as an anti-tissue wrapping bearing thereby helping to prevent tissue binding, and as a bearing to the cutter.

FIG. 25 illustrates a known prior art single-use biopsy device as disclosed in U.S. Pat. No. 4,699,154 and Re. 34,056, both previously incorporated herein by reference. It should be noted that this embodiment is merely representative of many different types of such devices currently or potentially available, any of which would be suitably used in conjunction with the inventive embodiments. However, the illustrated embodiment is illustrative and will serve as a good point of reference.

In the device 94, a needle assembly 96 comprises a hollow outer cutting cannula or needle 98 and an inner piercing needle 100. The needles 98 and 100 are pointed at their distal end, and the inner needle 100 is also provided with a tissue receiving notch 102 at its distal end for receiving the tissue sample. At their proximal ends, the needles 98 and 100 are provided with heads 104 and 106, respectively, for mounting within the housing 108 of the sampling device. A front slide 110 and a rear slide 112 are slidably provided along the axial direction of the housing 108. Each slide 110 and 112, respectively, is actuated by at least one spring 114 and 116, respectively, biasing the respective slide in a distal direction. The spring 114 acts between a stop 118 provided on the slide 110 and a fixed transverse wall (not shown) in the housing 108. The spring 116 acts between a stop on the slide 112 and the rear end wall 120 of the housing 108. In the housing 108, there are two parallel slide bars or guide rods 122, 124 on which the slides 110, 112 run.

The front slide 110 may be retained in a proximally withdrawn position by means of a hook provided on a tongue member 126 protruding from the slide, the tongue member engaging the bottom edge of the aforementioned traverse wall (not shown). The rear slide 112 may in a corresponding way be hooked and retained in a withdrawn position by means of a hook 128 protruding from the slide, which in turn engages a springy hook member 130 at the rear wall 120 of the housing.

The tissue sampling device 94 is loaded and released in the following manner. In the unloaded initial position, the slides 110, 112 are each biased distally (toward the left) by the springs 114, 116, respectively. To load the device, the needle assembly 96, in which the inner needle 100 is freely slidable in the hollow outer cannula 98, is moved proximally (to the right) and placed in the correct position in the housing 108, so that the needle heads are engaged into the slides 110, 112, which are configured to receive them, such that each needle head 104, 106 follows the movements of the slides 110, 112, respectively.

Thus, when the needle assembly 96 has been placed in the device, the device is energized in that the slides 110, 112 are moved simultaneously to their latched positions, whereby the springs 114, 116 are compressed and would act to return the slides 110, 112 to their initial position if released from the latching hooks 126, 128, and 130.

When the needle assembly 96 has been positioned at the desired tissue location, the sampling is carried out by pressing a release button 132, whereby the engagement between the hooks 128 and 130 is interrupted. Because of the biased spring 116, the slide 112 together with the inner needle 100 is thus pushed distally toward the left to its initial position. For a short period of time, the slide 110, together with the outer cannula 98, is still retained in its energized position. Thus, the inner piercing needle 100 protrudes from the outer cannula 98, thereby exposing the notch 102. Immediately after having reached its initial position, however, the slide 112 impacts and abuts the hook spring (tongue member) 126, and interrupts the engagement of the hook with the transverse wall (not shown), whereby the spring 114 also pushes back the slide 110 distally to its initial position. Consequently, the outer cannula 98 again is pushed over the side facing notch 102 in the inner needle 100, thereby severing the tissue sample that has prolapsed into the notch. Thereafter the needle assembly 96 is withdrawn from the tissue and removed from the sampling device, following which the sample is analyzed.

While such a device works fairly well for its intended purposes, as discussed in the Background of the Invention, there are a number of problems inherent in their operation. Most significantly, there is no positive means for engaging the tissue sample within the notch 102, particularly since no source of vacuum is available, as in the embodiments of FIGS. 1–24, to assist in collection of the tissue. Consequently, several inventive embodiments including mechanical elements for capturing the tissue are disclosed herein, each of which dramatically improve the quality and quantity of the tissue samples collected, on a consistent basis.

Figure 26:
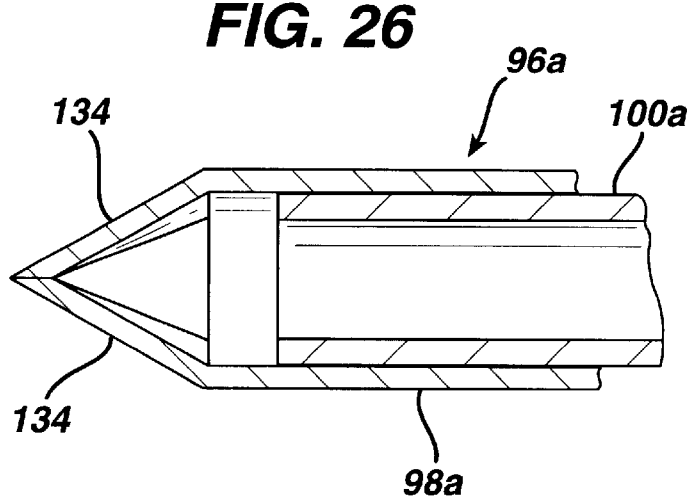
FIG. 26 is a fragmentary cross-sectional view of a modified needle assembly for a biopsy gun of the type illustrated in FIG. 25, illustrating the needle assembly in a first position for advancing the needle assembly through tissue to a selected tissue sample site.
Figure 27:
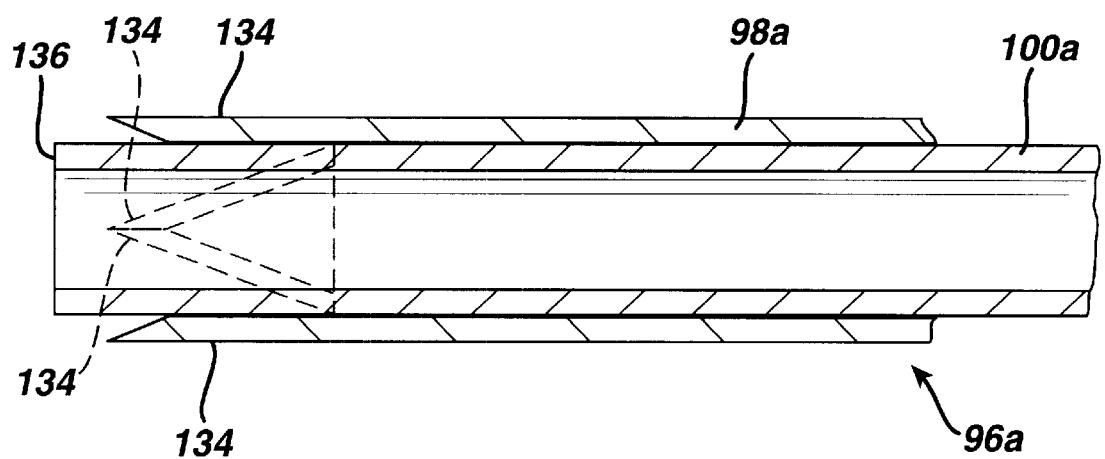
FIG. 27 is a fragmentary cross-sectional view of the needle assembly illustrated in FIG. 26, showing the needle assembly, in a second position for obtaining and cutting a tissue sample.
Figure 28:
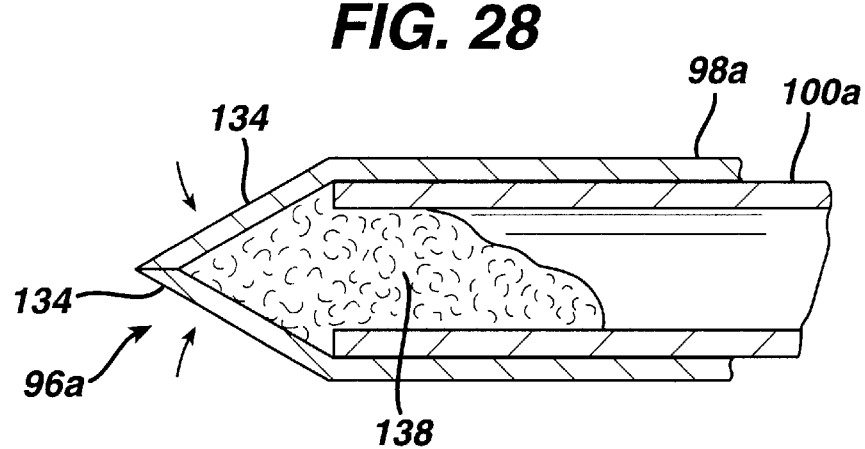
FIG. 28 is a fragmentary cross-sectional view of the needle assembly illustrated in FIG. 26, showing the needle assembly in a third position wherein the tissue sample has been severed and is contained in the tissue receiving port of the needle assembly.
Figure 31:
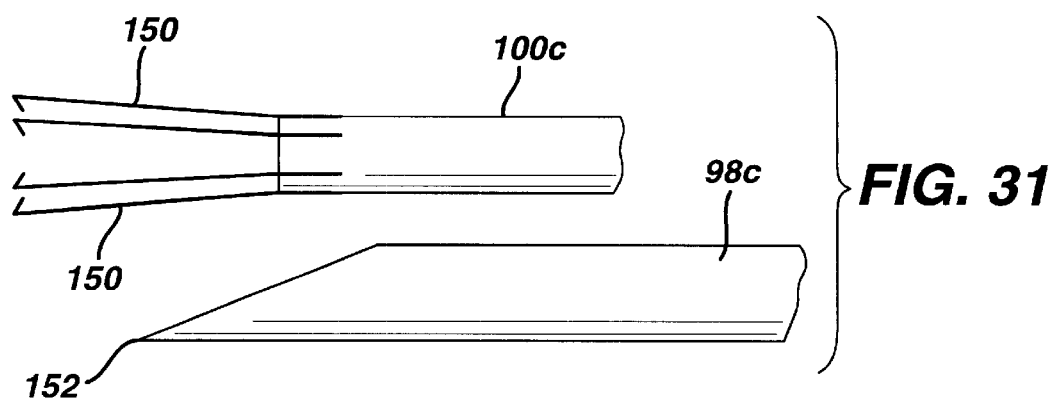
FIG. 31 is a schematic exploded view of a third modified needle assembly for a biopsy gun of the type illustrated in FIG. 25.

Referring now to FIGS. 26–28, a modified embodiment of the needle assembly 96 of FIG. 25 is illustrated, wherein like elements are designated by like reference numerals, followed by an a. In this embodiment, in their initial position, as shown in FIG. 26, with both springs energized, the inner needle 100*a* is retracted within the outer cannula 98*a*, and cutter leaflets 134 are in a closed position on the distal end of the needle 98*a*. Preferably, there are two, four, or six cutter leaflets 134, which in the closed position come together to form a piercing cone. Of course, however, any number of leaflets may be employed within the scope of the invention.

FIG. 27 illustrates the intermediate position immediately after the release button 132 (FIG. 25) has been activated. At this juncture, the spring 116 propels the inner needle 100*a* distally, forcing the leaflets 134 open. The sharpened distal edges 136 of the needle 100*a* begin to-cut tissue, which is contained within the distal end portion of the needle 100*a*.

Then, upon release of the spring 114, the outer cannula 98a is propelled distally, as shown in FIG. 28, causing the leaflets 134 to snap closed to sever and contain the tissue sample 138.

It should be noted that this embodiment, while useful as a modification to the FIG. 25 device, may also be employed in the FIG. 1 device. In this instance, the inner needle 100a comprises a rotating cutter, which translates back and forth as previously described.

Figure 29:
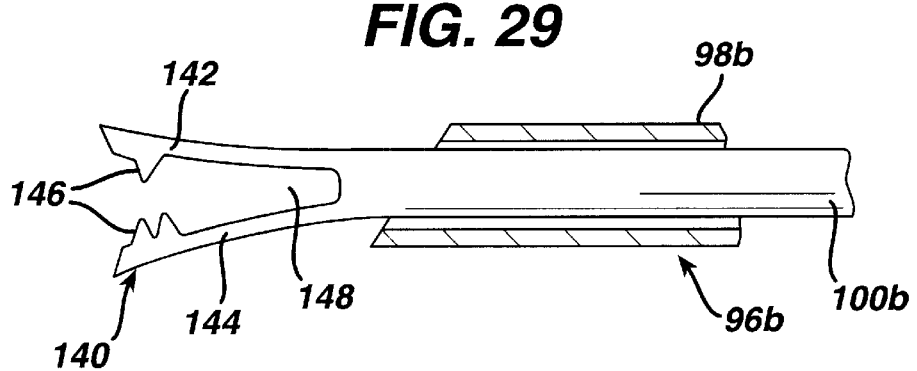
FIG. 29 is a fragmentary cross-sectional view of a second modified needle assembly for a biopsy gun of the type illustrated in FIG. 25, illustrating the needle assembly in a first position for advancement into the selected tissue sample site.
Figure 30:
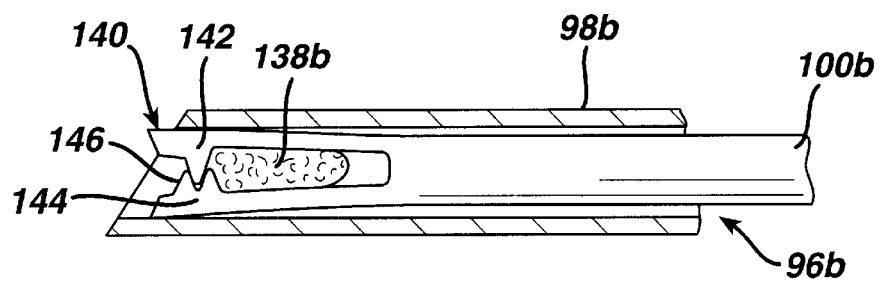
FIG. 30 is a fragmentary cross-sectional view of the needle assembly illustrated in FIG. 29, showing the needle assembly in a second position after capture of a tissue sample.

FIGS. 29 and 30 illustrate a second modified embodiment of the needle assembly in the FIG. 25 device. Again, like elements are designated by like reference numerals, followed by a b. In this embodiment, the inner needle 100b has been modified to include an "alligator" tip 140, which includes jaws 142, 144 and teeth 146. When the spring 116 is released, the inner needle 100b shoots distally and captures tissue in the opening 148 within the jaws 142, 144. Then, when the spring 114 is released, the outer cannula 98b shoots distally, severing tissue along the sides of the tissue sample opening 148 as it moves distally, and also forcing the jaws 142, 144 shut, so that they "bite off" the end of the tissue sample 138b, as illustrated in FIG. 30. This embodiment also may be adapted for use with the device of FIG. 1, if desired.

Figure 32:
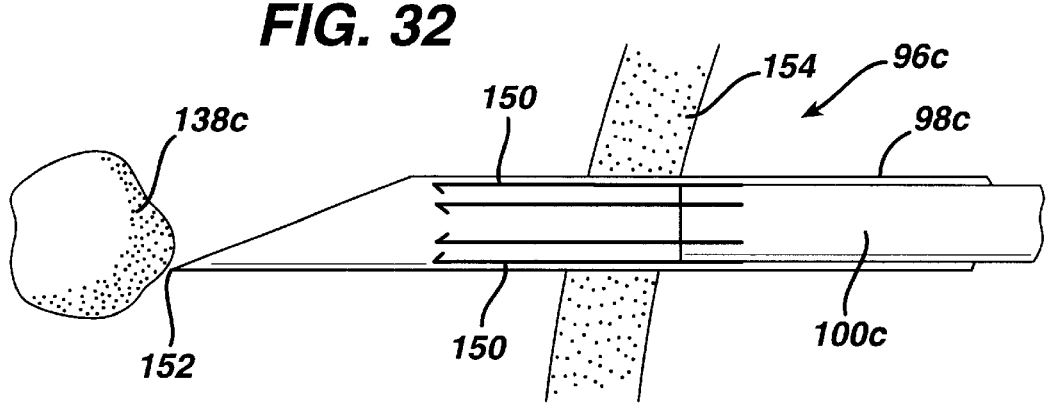
FIG. 32 is a schematic side elevational view of the needle assembly illustrated in FIG. 31, showing the assembly in a first position approaching a selected tissue sample.
Figure 33:
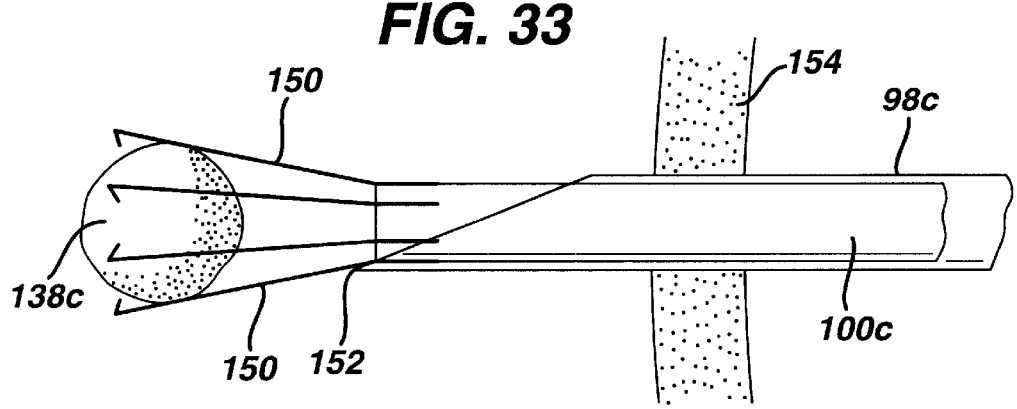
FIG. 33 is a schematic side elevational view similar to FIG. 32, illustrating the needle assembly in a second position grabbing the selected tissue sample.
Figure 34:
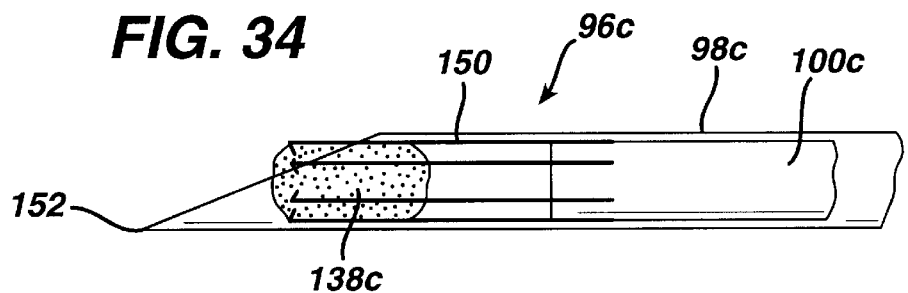
FIG. 34 is a schematic side elevational view similar to FIG. 32, illustrating the needle assembly in a third position after capture of the selected tissue sample.

Finally, FIGS. 31–34 illustrate a third modified embodiment of the needle assembly in the FIG. 25 device. In this embodiment, like elements are designated by like reference numerals, followed by a c. Like the FIG. 29 embodiment, the inner needle or "grabber" 100c has been modified, this time to include a plurality of hooked extractors 150 extending from its distal end. The outer cannula 98c includes a sharpened cutter point 152. In operation, initially the grabber 100c is retracted into the cutter 98c while the device is in its energized state, the point 152 being used to pierce the body wall 154 as the device is guided to the desired tissue sample 138c (FIG. 32). Then, as illustrated in FIG. 33, the grabber 100c is shot distally by means of the release of spring 116. As it travels distally, the hooked extractors 150 become extended and latch onto the tissue sample 138c. Then, once the second spring 114 is released, the cutter 98c shoots distally, collapsing the hooked extractors 150 and severing the tissue sample, which is received into the lumen of the cutter 98c.

This embodiment, as well, may be adapted for use with the device illustrated in FIG. 1. Furthermore, while four extractors 150 are shown, in actuality any desired number may be employed, as long as they may be fully retracted within the cutter 98c.

While this invention has been described with respect to various specific examples and embodiments, it is to be understood that the invention is not limited thereto and that it can be variously practiced within the scope of the following claims.

What is claimed is:

1. A biopsy instrument, comprising:

an elongate hollow outer piercing needle having a lumen, a sharpened distal end for piercing tissue, and a lateral opening located proximal to said sharpened distal end for receiving a portion of a tissue mass positioned adjacent to said lateral opening;

an elongate inner cutting cannula having a lumen and being disposed coaxially and slidable within said elongate outer piercing needle, said elongate inner cannula having a sharpened distal end for cutting the portion of tissue protruding into said elongate outer piercing needle lateral opening when said elongate inner cannula slides distally past said lateral opening, thereby depositing the portion of cut tissue within said elongate inner cannula proximal to said sharpened distal end;

a vacuum generator for generating a vacuum pressure which fluidly communicates with said lateral opening through said inner cannula lumen; and a tissue stop device disposed in the lumen of said inner cannula and having a structure disposed proximally of said lateral opening which is adapted to sufficiently obstruct said lumen so that a tissue sample drawn into the lateral opening by said vacuum pressure and severed by the cutting cannula is prevented from migrating proximally through the cutting cannula lumen.

2. A biopsy instrument as recited in claim 1, wherein said tissue stop device comprises a linear wire disposed along said inner cannula lumen from the distal end thereof, the proximal end of the wire being configured to comprise said obstruction structure.

3. A biopsy instrument as recited in claim 2, wherein said obstruction structure comprises a corkscrew position of said wire, the cross-sectional width of the corkscrew portion being just slightly smaller than the internal diameter of said cutter lumen.

4. A biopsy instrument as recited in claim 2, wherein the distal end of said wire comprises a tip which is fixedly attached to the distal end of the hollow outer piercing needle.

* * * * *